United States Patent [19]

Carlsson

[11] Patent Number: 4,631,581
[45] Date of Patent: Dec. 23, 1986

[54] METHOD AND APPARATUS FOR MICROPHOTOMETERING MICROSCOPE SPECIMENS

[75] Inventor: Kjell S. Carlsson, Vallentuna, Sweden

[73] Assignee: Sarastro AB, Stockholm, Sweden

[21] Appl. No.: 703,842

[22] Filed: Feb. 21, 1985

[30] Foreign Application Priority Data

Mar. 15, 1984 [SE] Sweden ................................ 8401458

[51] Int. Cl.$^4$ ............................................. H04N 7/18
[52] U.S. Cl. ...................................... 358/93; 356/308; 356/318; 358/107
[58] Field of Search ..................... 358/93, 106, 107, 89; 356/226, 301, 308, 318; 350/511; 250/234

[56] References Cited

U.S. PATENT DOCUMENTS

| | | | |
|---|---|---|---|
| 4,141,032 | 2/1979 | Haeusler | 358/89 |
| 4,194,217 | 3/1980 | van den Bosch | 358/93 |
| 4,218,112 | 8/1980 | Ruker | 250/234 |
| 4,223,354 | 9/1980 | Noble | 356/308 |
| 4,407,008 | 9/1983 | Schmidt | 356/301 |

*Primary Examiner*—Howard W. Britton
*Attorney, Agent, or Firm*—Sughrue, Mion, Zinn, Macpeak and Seas

[57] ABSTRACT

A method for microphotometering individual volume elements of a microscope specimen 10, comprising generating a luminous dot or cursor and progressively illuminating a plurality of part elements in the focal plane 11 of the microscope through the specimen. The mutual position between the specimen and the focal plane is then changed and a plurality of part elements in the focal plane are illuminated. Reflected and/or fluorescent light and transmitted light respectively created by the illumination is collected, detected and stored for generating a three-dimensional image of that part of the specimen composed of the volume elements. Illumination of multiples of part elements is implemented by deflecting the cursor and/or by moving the specimen. The change in the relative mutual position between the specimen and the focal plane of the microscope is effected either by displacing the specimen or the objective. Apparatus for carrying out the method include a specimen table 301, a microscope objective and light source 31-32-33. The table or the objective are arranged for stepwise movement along the main axis of the microscope synchronously with punctilinear light scanning of the specimen. The table is arranged for stepwise movement at right angles to the main axis and/or the light source is arranged for deflection over the focal plane 21 through the specimen.

9 Claims, 7 Drawing Figures 4,631,581

METHOD AND APPARATUS FOR MICROPHOTOMETERING MICROSCOPE SPECIMENS

TECHNICAL FIELD

The invention relates to a method for microphotographing prepared specimens and displaying the resultant images thereof, by generating with the aid of a convergent light beam a luminous dot or cursor in the focal plane of a microscope, matching the cursor with a plurality of part elements in the prepared specimen, collecting the light created by the cursor and the prepared specimen, detecting the collected light, and generating corresponding electric signals. The invention also relates to apparatus for carrying out the method.

BACKGROUND ART

Qualitative and quantitative microscopic investigations (study assays) of prepared specimens of the human body and of animals constitute an important and time-consuming part of research work, for example, within the field of medicine. For example, when wishing to make a close study of a liver there is first prepared a given number of thin specimens of the liver to be examined (these specimens being prepared with the aid of a microtome), whereafter the specimens are subjected to a qualitative and quantitative examination under a microscope. A picture of the general condition of the liver, changes in its state of disease, etc., can then be obtained by combining the results of the assays.

It is also known to obtain the assay result from a plurality of locations on the surface of a microscope specimen with the aid of electronic scanning techniques.

When applying known techniques it is still necessary in general to prepare a relatively large number of specimens (sections) from the subject to be examined, which is expensive, time-consuming and highly laborious. The object of the present invention is to simplify and, in many instances, even to refine the methodology of effecting such microscopic investigations, and at less cost.

SUMMARY OF THE INVENTION

The method according to the invention comprises producing a three-dimensional image of a volume of a microscope specimen (i.e. a specimen for microscopic study) taking a starting point from the method described in the introduction, and is mainly characterized by changing the mutual relative positions of the specimen and the focal plane and renewed matching of the cursor or luminous dot with a plurality of part elements in the specimen; collecting light created by the cursor and part elements in the specimen; and screening-off any synchronous disturbing light created by adjacent (above, beneath, beside) part elements in the specimen; detecting the light thus collected and storing the measurement values resulting from said detection, the storage of the measurement values being effected synchronously with the matching of the cursor with the part elements in the specimen and the change in the relative mutual positions of the specimen and the focal plane, the measurement values being representative of locations in various layers through the specimen; and collecting the measurement values derived from locations in a plurality of layers representative of a given volume of the specimen in dependence upon upon planned/desired analysis of the specimen.

The aforesaid measurement values together give a detailed description or picture of the whole of the volume determined through all of said plurality of locations. By converting the measurement values to digital form and storing the same in the memory of a data processor, it is possible to produce three-dimensional images suitable for assay and further analysis.

Thus, it is possible—without preparing fresh physical specimens—to study the specimen on a data screen from different projections and to combine two such projections to obtain a stereoscopic image. This enables the person carrying out the investigation to produce in a very short time precisely those views and incident angles which may be desired as the investigation proceeds.

The study of nerve cells is an example of an area in which the method according to the invention is particularly well suited. Nerve cells exhibit an extremely large number of branches and present a complicated three-dimensional structure. Investigatory studies of such structures with the aid of traditional microscope equipment are extremely difficult to carry out and are also very time-consuming. In addition the information obtained therefrom is incomplete. Corresponding studies carried out in accordance with the invention have been found to provide abundantly more information than that obtained when carrying out the studies in accordance with known methods. Other possible areas where the three-dimensional structure is of great interest include studies of the inner structures of cells, for example a study of the configuration of the cell core, chromosomes etc.

The illumination and registration technique according to the invention affords the following advantages. It is possible to select a thin section from the specimen for registration and to combine several such sections to produce a three-dimensional image. The images are made richer in contrast and clearer by decreasing the level of stray light. Sensitive and delicate specimens are protected from harm, because the total light exposure is low.

BRIEF DESCRIPTION OF THE DRAWINGS

The invention will now be described in more detail with reference to the accompanying schematic drawings, in which.

DETAILED DESCRIPTIONS OF THE PREFERRED EMBODIMENTS

Figure 1:
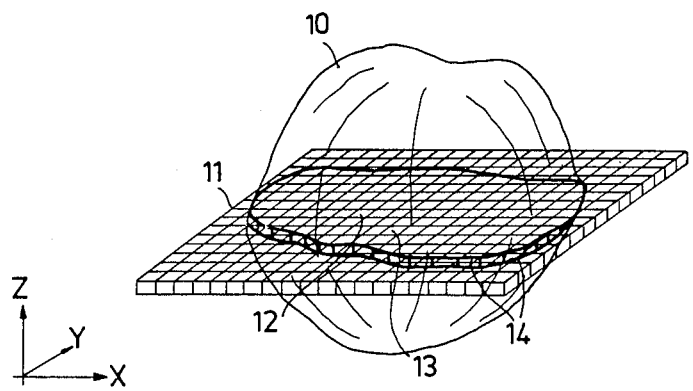
FIG. 1 illustrates in perspective the contour of a specimen and a section laid through the specimen.

In FIG. 1 the reference 10 identifies a microscope specimen through which there is laid an imaginary horizontal section comprising a plurality of part elements: for reasons relating to the technicalities of the drawing the section exhibits 20 rows in the x-direction and 15 rows in the y-direction, i.e. a total of 300 part elements, such as part elements 12 and 13 for example, but may in practice of course exhibit many more or far less elements and with sections of a different form, such as square or elongated rectangular sections for example, depending entirely upon the form of the specimen.

When microphotometering a microscope specimen, 75, 100 or may be 200 such imaginary sections may be envisaged in practice, these sections being plane parallel and bordering upon one another, two and two, or spaced equidistantly from one another. That part of the section 11 which lies within the specimen 10 has been shown in the figure with a thicker line 14.

Figure 2:
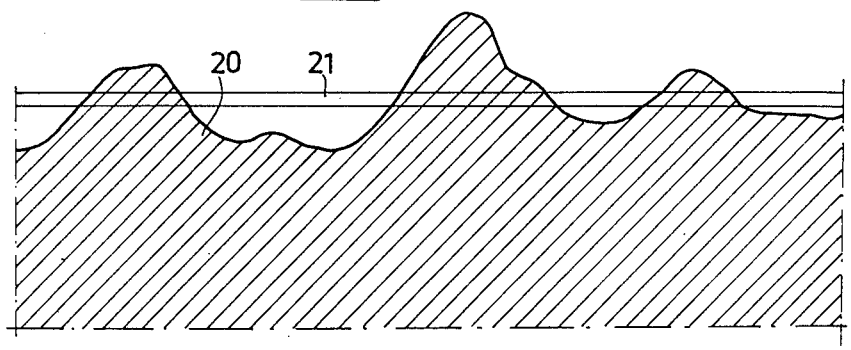
FIG. 2 is a vertical sectional view of a specimen with a section according to FIG. 1 laid in the surface structure of the specimen.

The specimen 20 illustrated in vertical sections in FIG. 2 constitutes part of a material surface to be studied. A section 21, corresponding to the section 11 in FIG. 1, is placed in the upper part of the specimen and is thus here seen from the side. The two indicated sections 11 and 21 are representative of what is referred to hereinafter as "the focal plane".

Figure 3:
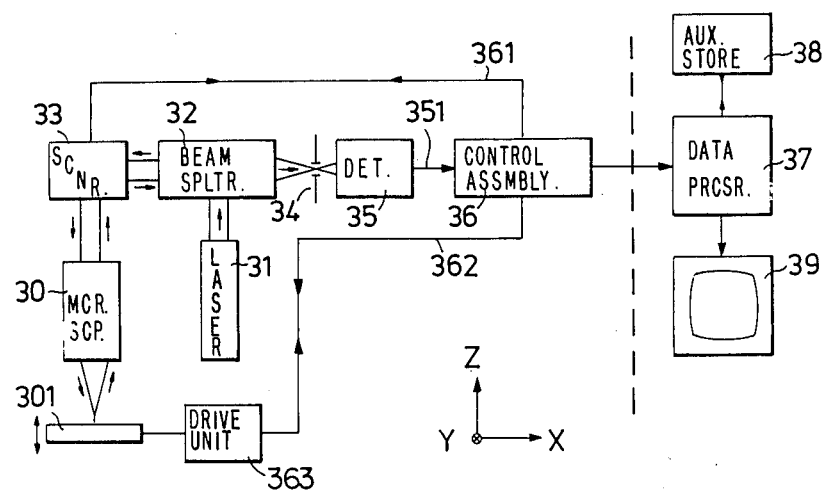
FIG. 3 illustrates apparatus for microphotometering a microscope specimen while using reflected and/or fluorescent light, comprising a two-dimensional scanner and a vertically movable object table.

The apparatus illustrated in FIG. 3 includes a microscope 30 having an object table 301, a laser-light source 31 for producing a beam of light through a beam-splitting unit 32, and a scanner 33 operative in panning the beam of light to a plurality of locations in the focal plane (x-y-plane) of the microscope 30, an aperture 34, and a control and data-collection assembly 36 for controlling, inter alia, the scanner 33 via a line 361, and for collecting electric signals deriving from reflected and-/or fluorescent light arriving at the detector 35 after having passed from the object table 301 through the microscope 30, the scanner 33 and the aperture 34, this light being converted in the detector 35 to electric signals which are transferred through the line 351 to the control assembly 36, and finally externally located equipment for storing, processing and visually displaying data originating from said signals, this equipment comprising a data processor 37 and an auxiliary store 38, and a display screen 39 connected to the data processor 37.

A luminous dot or cursor created by the light beam from the laser source 31 is deflected by the scanner 33 to a number of positions in a specimen placed on the object table 301, in the focal plane, which focal plane may be the section indicated in FIG. 1. Stray light, possibly eminating from locations (volume elements) above, beneath or beside the location in the x-y-plane just scanned by the scanner 33, is excluded by the aperture 34 and is caused to deliver information relating to its characteristics through, for example, reflected light. When a location has been scanned a control pulse is delivered from the control assembly 36 to the scanner 33, via the line 361, and the scanner therewith reflects the beam to the next location (e.g. an x-square) in the same row (y-row), this procedure being continued until the whole of section 11 has been scanned or sensed. The object table 301 is thereupon moved stepwise (up or down) in response to a control pulse (signal) fed from the control assembly 36 to a drive unit 363 via the line 362, which drive unit guides directly movement of the table 301 in the z-direction. The object table with the specimen thereon is thus displaced through a given distance in the z-direction, whereupon the focal plane of the microscope 30 will obtain a new position through the specimen, this new position being scanned in the same manner as that previously described. The whole of the specimen is thus scanned in this way successively at equidistant locations along equidistant parallel lines in equidistant planes. Signals are transferred from the scanner 33 and the drive unit 363 respectively to the control assembly 36, bearing information relating to the current position of the cursor created by the light beam (x-y-direction) and of the table 301 (z-direction).

When creating a three-dimensional picture of a volume of a microscope specimen with the aid of the apparatus just described, the following operational steps are taken:

a luminous dot or cursor is created in the focal plane 11 of the microscope 30, this plane passing through the specimen;

the cursor is deflected to a plurality of locations in the focal plane 11;

the mutual relative positions of the specimen and the focal plane 11 are changed and deflection of the cursor to a plurality of locations in the focal plane is renewed:

the change in the relative mutual positions of the specimen and focal plane is repeated stepwise, and after each such change the luminous cursor is again deflected to a number of locations in the focal plane;

the light created by the luminous cursor and part elements of the specimen is collected, this light carrying information relating to locations in the specimen, and any disturbing light eminating synchronously from adjacent locations is screened-off; and the thus collected light is collected and the measurement values obtained through said detection are stored, the storage of the measurement values being effected synchronously with the deflection of the luminous cursor in the focal plane and with the change in the mutual position between the specimen and the focal plane.

In this way there is obtained a description or picture of the whole of the volume of the specimen comprising the individual volume elements (the locations), this being achieved in an extremely short period of time. By way of example it can be mentioned that when microphotometering a specimen through approximately 100 sections and having $256^2$ measurement values (locations) in each section, the actual apparatus time is approximately 10 minutes. In addition to the highly simplified preparation of the specimen, however, it is also possible to produce through the data processor 37 three-dimensional images with selectable projection directions and with the possibility of making volumetric measurements.

Figure 4:
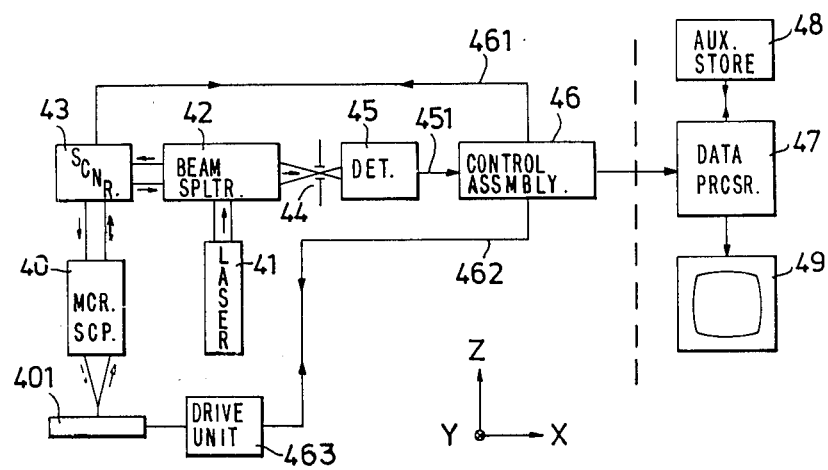
FIG. 4 illustrates the apparatus according to FIG. 3 modified with a single-dimension scanner and a vertically and laterally adjustable table.

The apparatus illustrated in FIG. 4 coincides with the apparatus illustrated in FIG. 3 with the exception that deflection caused through the scanner 43 is effected only in one direction (e.g. the y-direction), while the object table 401 is moved stepwise in the horizontal direction (x-direction) subsequent to the light beam having been advanced along a whole row or line and been displaced stepwise in a vertical direction (z-direction) subsequent to the light beam having been advanced along a whole section. This modification may be suitable when studying specimens of substantially elongated rectangular shape.

With the aforegiven exceptions in the functioning of the apparatus, the corresponding circuits and devices illustrated in FIGS. 3 and 4 are identified by reference numerals differing only in their first digits.

Figure 5:
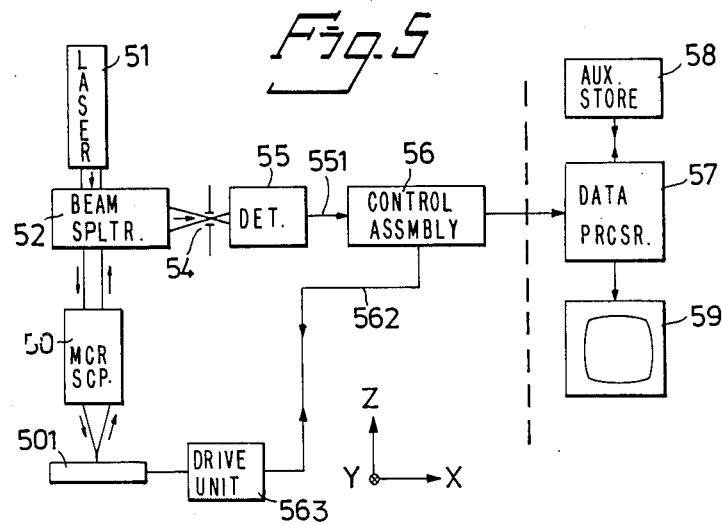
FIG. 5 illustrates the apparatus according to FIG. 3 which lacks the scanner but has an object table which can be moved in three dimensions.

The apparatus illustrated in FIG. 5 coincides with that illustrated in FIG. 3 with the exception that the scanner 33 is omitted totally and the object table 501 is instead arranged to be moved stepwise along a surface in the horizontal plane (x-y-plane) and stepwise in a vertical direction (z-direction). These movements are controlled from the drive unit 563 which receives, in turn, synchronizing pulses from the control assembly 56.

Mutually corresponding circuits and devices in FIGS. 3 and 5 are identified by reference numerals differing only in their first digits.

Figure 6:
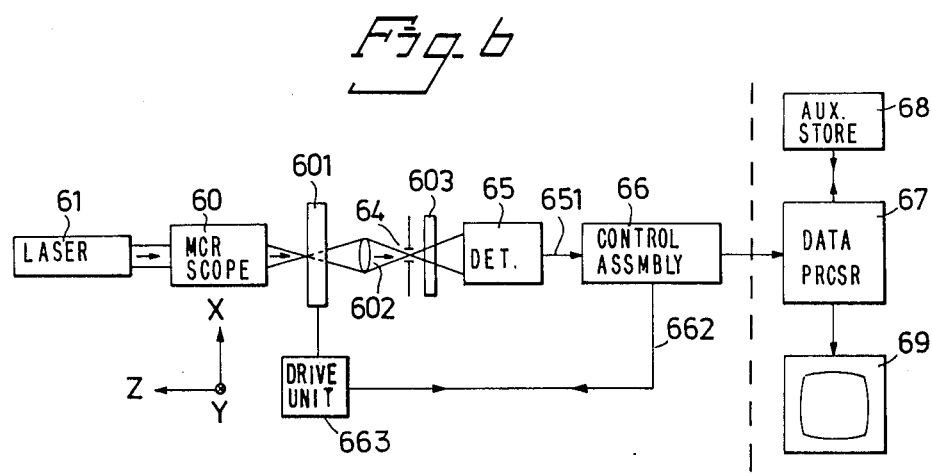
FIG. 6 illustrates the apparatus according to FIG. 5 modified for transmitted or fluorescent light.

The apparatus according to FIGS. 3-5 are intended to utilize reflected and/or fluorescent light from the specimen. It is also possible to work with transmitted light, however, and the apparatus illustrated in FIG. 6 is intended for this case. Light from the laser 61 passes the microscope 60 and is focused on a point in the focal plane in a specimen placed on the object table 601. The light allowed to pass through or excited (fluorescence) by the specimen at the point in question is collected by an objective 602 and permitted to pass an aperture 64 and, in the case of fluorescence, a filter 603 to eliminate exiting laser light, whereupon detection is effected in the detector 65 (conversion to electric signals and analogue/digital conversion) and collection in the control and data collecting assembly 66 in the aforedescribed manner. In a manner similar to that described with reference to FIG. 5, the object table 601 is also caused to move stepwise, in response to control signals from the assembly 66, along a line or row in a surface plane (x-y-plane) and in a direction (z-direction) perpendicular to the surface plane. The function of the apparatus is similar in other respects to the function of the previously described apparatus.

The various remaining circuits or devices in FIG. 6 corresponding to the circuits or devices in FIG. 5 are identified by reference numerals differing only in their first digits.

The invention is not restricted to the aforedescribed and illustrated embodiments. For example, although the methods forming the basis for the apparatus illustrated in FIGS. 3 and 4, see also the following claims 2 and 3, probably give optimal results in respect of reflected light, modifications can be made in principle for the use of transmitted light. In addition, the drive units 363, 463 and 563 of respective apparatus according to FIGS. 3-5 can also be used to advantage for controlling movement of the microscope objective in z-directions instead of respective object tables 301, 401 and 501. There is obtained in both instances (fixed objective, movable object table in z-direction; movable objective in z-directions, fixed object table in z-directions) a change in the mutual distance between the specimen 10 and the focal plane 11.

In the aforegoing mention has been made as to how the light beam is stepped forward along a line on (in) the specimen with the aid of control signals from the control assembly (e.g. 36 in FIG. 3). Modifications may be made, however, to enable the light beam to be swung continuously forwards and backwards for example, but so that detection of the reflected signal takes place exactly at moments in time corresponding to given positional locations in the focal plane in the specimen.

It has been mentioned in the aforegoing that images in selectable projections can be readily obtained once the specimen has been microphotometered in accordance with the invention.

Figure 7:
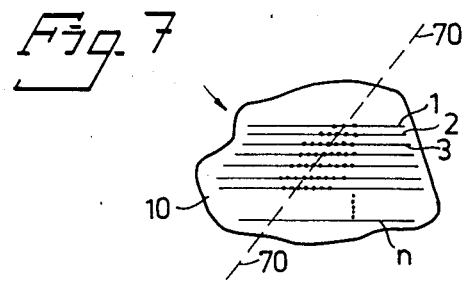
FIG. 7 illustrates a specimen in which a plurality of sections have been laid.

FIG. 7 illustrates schematically a specimen 10 through which sections 1-n have been laid (at right angles to the plane of the drawing) in accordance with the invention. A researcher who during the course of his/her work finds that he needs to view a section through a given part of the specimen from a different angle, e.g. through sections 70—70, is able to immediately obtain from the measurement value equipment an image comprised of measuring results from a plurality of sections 1-n, and with a starting point from this view image can then find reason to concentrate his/her interest to another part of the specimen, perhaps along an additional section. The possibilities are manifold and afford a high degree of flexibility in respect of research work.

I claim:

1. A method for microphotometering and subsequent image combination by generating with the aid of a convergent light beam a luminous dot or cursor in the focal plane (11) of a microscope (30), fitting the cursor to a plurality of part elements in the specimen (10), and collecting light created by the luminous cursor and the specimen (10), detecting the collected light and producing corresponding electric signals, characterized by changing the mutual position between the specimen (10) and the focal plane (11) and re-fitting the luminous cursor to a plurality of part elements in the specimen (10); repeating stepwise changes in the mutual position between the specimen (10) and the focal plane (11) and, subsequent to each such change, again fitting or matching the luminous cursor to a plurality of part elements in the specimen; collecting the light created by the luminous cursor and part elements in the specimen (10) and screening-off any disturbing light created synchronously from adjacent (above, beneath, beside) part elements in the specimen (10); detecting the thus collected light and storing measurement values obtained through said detection, said storage optionally being effected synchronously with the matching of the luminous cursor with part elements in the specimen (10) and with the changes in the mutual position between the specimen (10) and the focal plane (11), said measurement values being representative of locations in various layers through the specimen; and combining the measurement values from locations in a plurality of layers, representative of a given volume of the specimen, in dependence upon a planned/desired analysis of the specimen.

2. A method according to claim 1, characterized in that matching of the luminous cursor with a plurality of part elements in the specimen (10) is effected by delinking stepwise the convergent light beam in two dimensions (x- and y-directions); and in that the stepwise change in the mutual position between the specimen (10) and the focal plane (10) of the microscope is effected by moving stepwise the microscope object table (301) on which the specimen is placed (z-direction).

3. A method according to claim 1, characterized in that matching of the luminous cursor with a plurality of part elements in the specimen (10) is effected by relatively rapid stepwise deflection of the convergent light beam in one dimension (y-direction), and by relatively slow stepwise displacement of the microscope object table (401) on which the specimen (10) is placed in a further dimension (x-direction); and in that the stepwise change in the mutual position between the specimen (10) and the microscope focal plane (10) is effected by stepwise displacement of the microscope object table (401) (z-direction).

4. A method according to claim 1, characterized in that matching of the luminous cursor with a plurality of part elements in the specimen (10) is effected by stepwise displacement of the microscope object table (501) along a surface (x-y-plane) perpendicular to the main axis of the microscope; and in that the stepwise change in the mutual position between the specimen (10) and the focal plane of the microscope (50) is effected by stepwise displacement of the object table (501) of the microscope (50) (z-direction).

5. A method according to claim 4, characterized in that collection of light (reflected fluorescent light) created by the luminous cursor and part elements in the specimen (10) is effected on that side of the object table (501) on which the microscope (50) is placed.

6. A method according to claim 5, characterized in that collection of light (transmitted light) created by the luminous cursor and part elements in the specimen (10) is effected on the opposite side of the object table (661) to that on which the microscope (60) is placed.

7. Apparatus for the microphotometering and subsequent image combination of a specimen, comprising a microscope (30) having an object table (301), a light source (31-32-33), a detector (35) and a control and data-collecting assembly (36), characterized in that the object table (301) of the microscope (30) is arranged for stepwise movement in a direction corresponding to the main axis (z-direction) of the microscope (30), said movement being controlled and effected in response to guide pulses from the control and data-collecting assembly (36) in synchronization with the scanning of the light source (31-32-33) of part elements in a microscope specimen (10) placed on the object table (301); and in that the apparatus also includes equipment (37,38,39) for storing, processing and visually displaying data originating from said measurements values.

8. Apparatus according to claim 7, characterized in that the object table (401) of the microscope (40) is arranged for stepwise movement in a first direction (x-direction) at right angles to the main axis of the microscope (z-direction); in that the light source (41-42-43) is arranged to scan stepwise part elements in the specimen in a further direction (y-direction) at right angles to the main axis of the microscope (z-direction); and in that movements of the object table (401) and the light source (41-42-43) are co-ordinated for scanning a first plurality of part elements in a first plane through the specimen, and then of a second plurality of part elements in a second plane through said specimen, said second plane extending plane parallel with the first plane, etc. for scanning the whole specimen.

9. Apparatus according to claim 7, characterized in that the object table (501) of the microscope (50) is arranged for relatively slow stepwise movement in a first direction (x-direction) at right angles to the main axis (z-direction) of the microscope (50) and in a relatively rapid stepwise movement in a further direction (y-direction) at right angles to the main axis (z-direction) of the microscope, wherewith movements of the object table (501) in planes at right angles to the main axis of the microscope and parallel with the main axis are co-ordinated through control pulses from the control and data-collecting assembly (56) for scanning part element after part element through the whole of the specimen.

* * * * *